United States Patent
Chakra et al.

(10) Patent No.: US 11,049,604 B2
(45) Date of Patent: Jun. 29, 2021

(54) COGNITIVE MONITORING OF ONLINE USER PROFILES TO DETECT CHANGES IN ONLINE BEHAVIOR

(71) Applicant: INTERNATIONAL BUSINESS MACHINES CORPORATION, Armonk, NY (US)

(72) Inventors: Al Chakra, Apex, NC (US); Faisal Ghaffar, Dunboyne (IE); Ahmad Abdul Wakeel, Dublin (IE); Kevin Carr, Raleigh, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 6 days.

(21) Appl. No.: 16/142,232

(22) Filed: Sep. 26, 2018

(65) Prior Publication Data

US 2020/0098467 A1 Mar. 26, 2020

(51) Int. Cl.
*G06F 15/173* (2006.01)
*G16H 20/70* (2018.01)
(Continued)

(52) U.S. Cl.
CPC ............ *G16H 20/70* (2018.01); *G06F 16/955* (2019.01); *G06F 16/9535* (2019.01); *H04L 67/22* (2013.01); *H04L 67/306* (2013.01)

(58) Field of Classification Search
CPC .................... G06Q 30/0269; G06F 11/3438
See application file for complete search history.

(56) References Cited

U.S. PATENT DOCUMENTS

| 4,658,370 A | 4/1987 | Erman et al. |
| 5,398,300 A | 3/1995 | Levey |

(Continued)

FOREIGN PATENT DOCUMENTS

| WO | 2016186362 A1 | 11/2016 | |
| WO | WO-2017023557 A1 * | 2/2017 | ......... G06F 19/3475 |

OTHER PUBLICATIONS

D. De Nart et al., "A Personalized Concept-Driven Recommender System for Scietific Libraries", Procedia Computer Science 38, 2014, pp. 84-91.

(Continued)

*Primary Examiner* — Umar Cheema
*Assistant Examiner* — Tesfu N Mekonen
(74) *Attorney, Agent, or Firm* — Cantor Colburn LLP; Teddi Maranzano (57) ABSTRACT

According to one or more embodiments of the present invention, a computer-implemented method includes creating a baseline online behavior profile of a user at a time t1 based on a usage of a social network by the user. The method further includes continuously monitoring an online behavior profile of the user on the social network and in response to detecting a deviation between the online behavior profile and the baseline online behavior profile, creating a changed online behavior profile of the user at a time t2, t2>t1. The method further includes extracting keywords from a plurality of online posts associated with the user, the online posts being from time t1 until time t2. The method further includes determining an event associated with the extracted keywords. The method further includes in response to the event being of a predetermined type, sending a notification to another user.

17 Claims, 8 Drawing Sheets

(51) Int. Cl.
*H04L 29/08* (2006.01)
*G06F 16/955* (2019.01)
*G06F 16/9535* (2019.01)

(56) References Cited

U.S. PATENT DOCUMENTS

| | | | |
|---|---|---|---|
| 6,067,539 A | 5/2000 | Cohen | |
| 7,587,387 B2 | 9/2009 | Hogue | |
| 8,719,302 B2* | 5/2014 | Bailey | G06F 16/95 |
| | | | 707/790 |
| 9,427,185 B2* | 8/2016 | Yom-Tov | G06F 16/951 |
| 10,109,171 B1* | 10/2018 | Mam | G08B 21/02 |
| 2010/0299339 A1 | 11/2010 | Kementsietsidis et al. | |
| 2012/0078837 A1 | 3/2012 | Bagchi et al. | |
| 2012/0136866 A1* | 5/2012 | Carter | G06Q 50/01 |
| | | | 707/740 |
| 2012/0301864 A1 | 11/2012 | Bagchi et al. | |
| 2013/0018652 A1 | 1/2013 | Ferrucci et al. | |
| 2013/0091147 A1* | 4/2013 | Kim | G06F 16/3334 |
| | | | 707/748 |
| 2013/0297536 A1* | 11/2013 | Almosni | G16H 50/20 |
| | | | 706/12 |
| 2014/0101247 A1* | 4/2014 | Pappas | H04L 67/22 |
| | | | 709/204 |
| 2014/0257852 A1* | 9/2014 | Walker | G06F 19/3456 |
| | | | 705/3 |
| 2014/0377727 A1* | 12/2014 | Yom-Tov | G16H 50/50 |
| | | | 434/236 |
| 2015/0347764 A1* | 12/2015 | Cornell | G06F 21/32 |
| | | | 726/28 |
| 2016/0012336 A1 | 1/2016 | Franceschini et al. | |
| 2016/0042371 A1* | 2/2016 | Klemm | G06Q 30/0203 |
| | | | 705/7.32 |
| 2016/0147970 A1* | 5/2016 | Rosen | G06F 16/242 |
| | | | 705/2 |
| 2016/0186362 A1 | 6/2016 | Mollart et al. | |
| 2017/0024656 A1* | 1/2017 | Gilon | G16H 20/10 |
| 2017/0046496 A1* | 2/2017 | Johnstone | G06F 19/00 |
| 2017/0126821 A1* | 5/2017 | Bostick | H04L 67/22 |
| 2018/0108237 A1* | 4/2018 | Gorzela | G08B 21/0423 |
| 2019/0052724 A1* | 2/2019 | Dancel | H04L 67/306 |
| 2019/0266242 A1* | 8/2019 | Arumugam | G06F 17/2785 |

OTHER PUBLICATIONS

D. McGuiness, "Question Answering on the Semantic Web", The Semantic Web, IEEE Computer Society, Jan./Feb. 2004, pp. 82-85.
D. McGuinness et al., "Trusting Answers on the Web", Knowledge Systems Laboratory, Stanford University, 20 pages.
P. Jansen et al., "A Study of Automatically Acquiring Explanatory Inference Patterns from Corpora of Explanations: Lessons from Elementary Science Exams", Conference on Neural Information Processing Systems, 2017, California, 7 pages.
P. Jansen et al., "Framing QA as Building and Ranking Intersentence Answer Justifications", Association for Computational Linguistics, vol. 43, No. 2, 2017, 43 pages.
P. Zerva et al., "Towards Design Support for Provenance Awareness: A Classification of Provenance Questions", ACM, Mar. 18-22, 2013, Italy, pp. 275-281.
R. Barzilay et aL, "A New Approach to Expert System Explanations", CoGenTex, Inc., pp. 78-87.
T. Goodwin et al., "Medical QUestion Answering for Clinical Decision Support", CIKM, Oct. 24-28, 2016, pp. 297-306.
W. Swartout et al., "Explanations in Knowledge Systems Design for Exlainable Expert Systems", DARPA Strategic Computing Initiative, IEEE, 1991, pp. 58-64.
Nandhini, et al., "Online Social Network Bullying Detection Using Intelligence Techniques," ScienceDirect, Procedia Computer Science 45 (2015): 485-492; 8 pages.
Weisz, Justin., "Segmentation and Classification of Online Chats," Computer Science Department, Carnegie Mellon University (2006); 8 pages.
Frey, et al., "Reality-Mining with Smartphones: Detecting and Predicting Life Events based on App Installation Behavior," Thirty Sixth International Conference on Information Systems, Fort Worth: 2015; 10 pages.

* cited by examiner

| Time | Sentiment Analysis Result | Avg. Frequency of Usage | Factorx1 | Factorx2 ... |
|---|---|---|---|---|
| 1 Jan 2017 | +ve | 10 hrs | ... | ... |
| 7 Jan 2017 | +ve | 12 hrs | | |
| 14 Jan 2017 | +ve | 11 hrs | | |
| .... | +ve | 8 hrs | | |
| .... | +ve | 10 hrs | | |
| 1 July 2017 | -ve | 40 hrs | | |

COGNITIVE MONITORING OF ONLINE USER PROFILES TO DETECT CHANGES IN ONLINE BEHAVIOR

BACKGROUND

The present invention relates to computing technology, and particularly cloud computing techniques for detecting the cause of user behavior change based on cognitive monitoring of online user profile, and especially changes in online behavior.

Different life events affect different people in different ways. Life events can include birth of a baby, death of friend/relative, job promotion, high workload at work, bullying, and any other social or personal event. In one or more examples, such events can affect mental health of a user (person). Typically, healthcare professionals are not aware of a user's experiencing episodes or symptoms until after the fact.

SUMMARY

According to one or more embodiments of the present invention, a computer-implemented method includes creating a baseline online behavior profile of a user at a time t1 based on a usage of a social network by the user. The method further includes continuously monitoring an online behavior profile of the user on the social network. The method further includes in response to detecting a deviation between the online behavior profile and the baseline online behavior profile, creating a changed online behavior profile of the user at a time t2, t2>t1. The method further includes extracting keywords from a plurality of online posts associated with the user, the online posts being from time t1 until time t2. The method further includes determining an event associated with the extracted keywords. The method further includes in response to the event being of a predetermined type, sending a notification to another user.

According to one or more embodiments of the present invention, a system includes an online social network, a memory, and a processor to monitor the online social network for a change in online behavior of a user when using the online social network by performing a method that includes creating a baseline online behavior profile of a user at a time t1 based on a usage of a social network by the user. The method further includes continuously monitoring an online behavior profile of the user on the social network. The method further includes in response to detecting a deviation between the online behavior profile and the baseline online behavior profile, creating a changed online behavior profile of the user at a time t2, t2>t1. The method further includes extracting keywords from a plurality of online posts associated with the user, the online posts being from time t1 until time t2. The method further includes determining an event associated with the extracted keywords. The method further includes in response to the event being of a predetermined type, sending a notification to another user.

According to one or more embodiments of the present invention, a computer program product includes a computer readable storage medium having stored thereon program instructions executable by one or more processing devices to perform a method that includes creating a baseline online behavior profile of a user at a time t1 based on a usage of a social network by the user. The method further includes continuously monitoring an online behavior profile of the user on the social network. The method further includes in response to detecting a deviation between the online behavior profile and the baseline online behavior profile, creating a changed online behavior profile of the user at a time t2, t2>t1. The method further includes extracting keywords from a plurality of online posts associated with the user, the online posts being from time t1 until time t2. The method further includes determining an event associated with the extracted keywords. The method further includes in response to the event being of a predetermined type, sending a notification to another user.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

It is understood in advance that although this disclosure includes a detailed description on cloud computing, implementation of the teachings recited herein is not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 1:
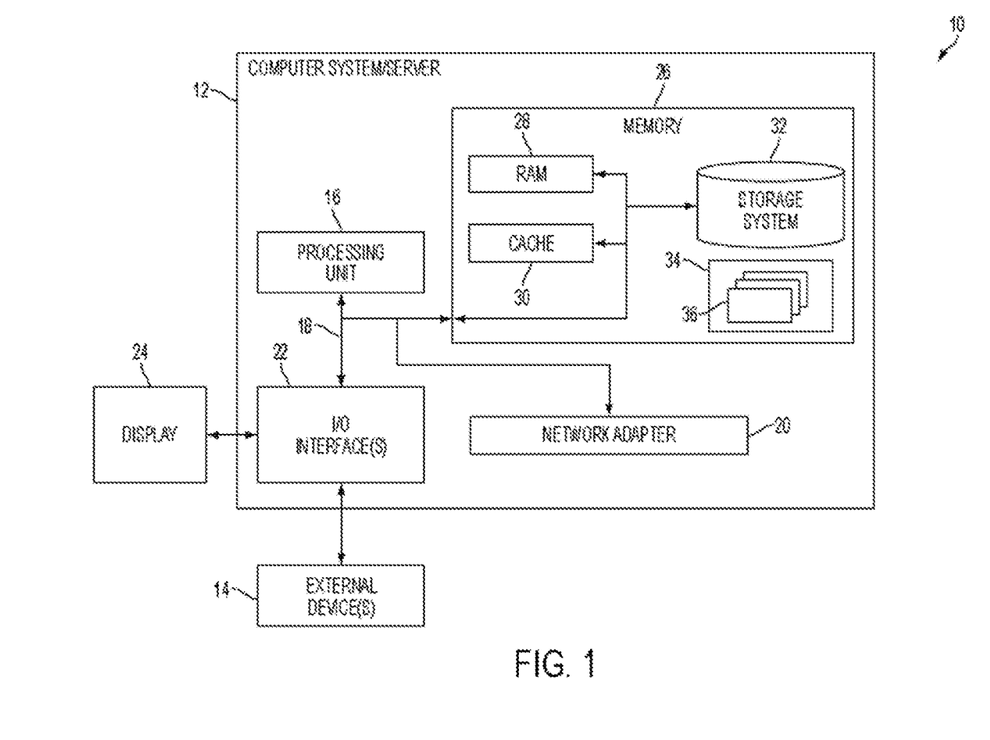
FIG. 1 depicts a cloud computing node according to one or more embodiments of the present invention.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 26, and a bus 18 that couples various system components including system memory 26 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 26 can include computer system readable media in the form of volatile memory, such as random access memory (RAM) 28 and/or cache memory 30. Computer system/server 12 may further include other removable/non-removable, volatile/non-volatile computer system storage media. By way of example only, storage system 32 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 26 may include at least one program product having a set (e.g., at least one) of program modules that are configured to carry out the functions of embodiments of the invention.

Program/utility 34, having a set (at least one) of program modules 36, may be stored in memory 26 by way of example, and not limitation, as well as an operating system, one or more application programs, other program modules, and program data. Each of the operating system, one or more application programs, other program modules, and program data or some combination thereof may include an implementation of a networking environment. Program modules 36 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
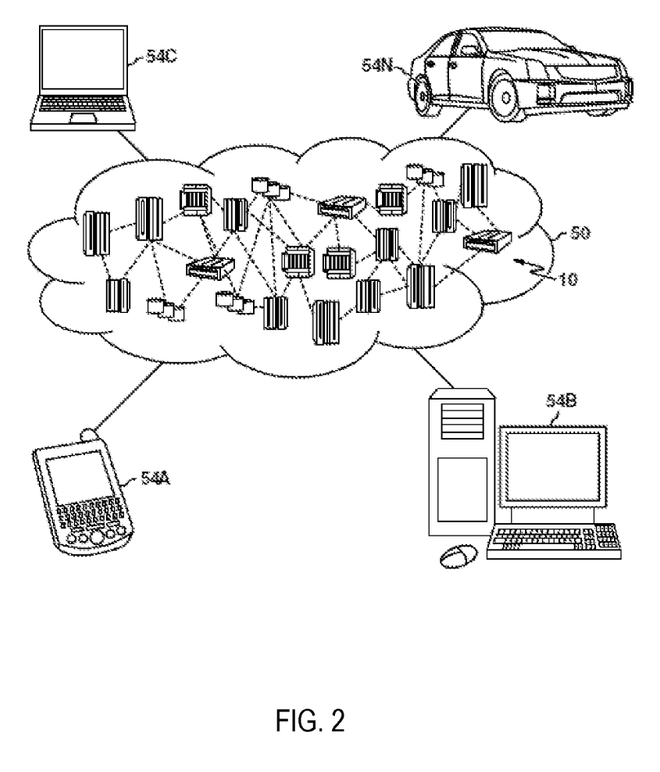
FIG. 2 depicts a cloud computing environment according to one or more embodiments of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
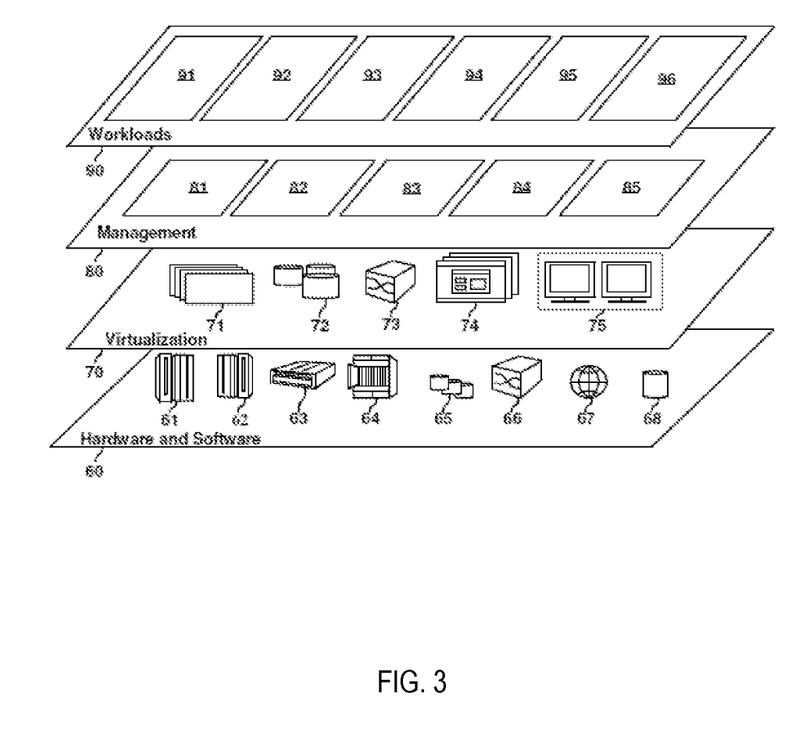
FIG. 3 depicts abstraction model layers according to one or more embodiments of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; social network monitoring 96 and the like.

As described earlier, typically, healthcare professionals are not aware of a user's experiencing episodes or symptoms until after the fact. Because, for example, the user may only see his/her healthcare professional weekly or bi-weekly. How the user responds to one or more life events can provide insights into the user's mental health. However, continuous monitoring of the user by a healthcare professional is not practically possible, physically and financially.

With the proliferation of communication devices, internet-of-things (IoT) devices, social networks, and ubiquitous computing networks, various data parameters of a user can be captured now, which was not possible to do in the past. Such data parameters collected continuously by electronic devices can be utilized to help address and solve the technical problem of monitoring the user's responses to one or more events. For example, wearable devices, such as FITBIT™ can be used to track sleep, heart rate, steps, and other such parameters. Further, with the use of "smart devices", such as smart TV and applications using content metadata, data parameters that are associated with the user and that can be collected and analyzed can include a number of movies watched, type(s) of movie watched, type(s) of music listened to, and the like. Further, smart microphone applications can monitor and provide a number of laughs e.g. LAUGH-O-METER™ or other audio cues regarding the user's stress level, for example ICALM™. It should be noted that above are just a few examples of data parameters that can be collected for a user and of one or more services that provide such monitoring. Embodiments of the present invention are not limited to any of the above data parameters and/or services, and different embodiments may use different data parameters/services.

According to one or more embodiments of the present invention, one or more data parameters of the user are continuously collected using technologies such as the examples above. Using the collected data parameters, a cognitive system is trained to detect a one or more life events happening in the user's life and further detecting a change in the user's online social behavior that can affect the user's behavior in the real-world. The user and the user's friends/relatives/healthcare professionals and other acquaintances can be notified of such a change in the user's behavior so that they can intervene as required.

In addition, such identification of life events can be used by other services, such as marketing services, to provide relevant services to the user based on the life event that has recently occurred. Marketing companies identify such life events presently, using methods like surveys, interviews, etc. to inquire about recent or upcoming life events in order to design their targeted marketing campaign. Such existing solutions for detecting life events are expensive, time-consuming, and not scalable. Using one or more embodiments of the present invention, such detection of life events can be performed at lesser cost and in lesser time compared to the existing solutions.

Figure 4:
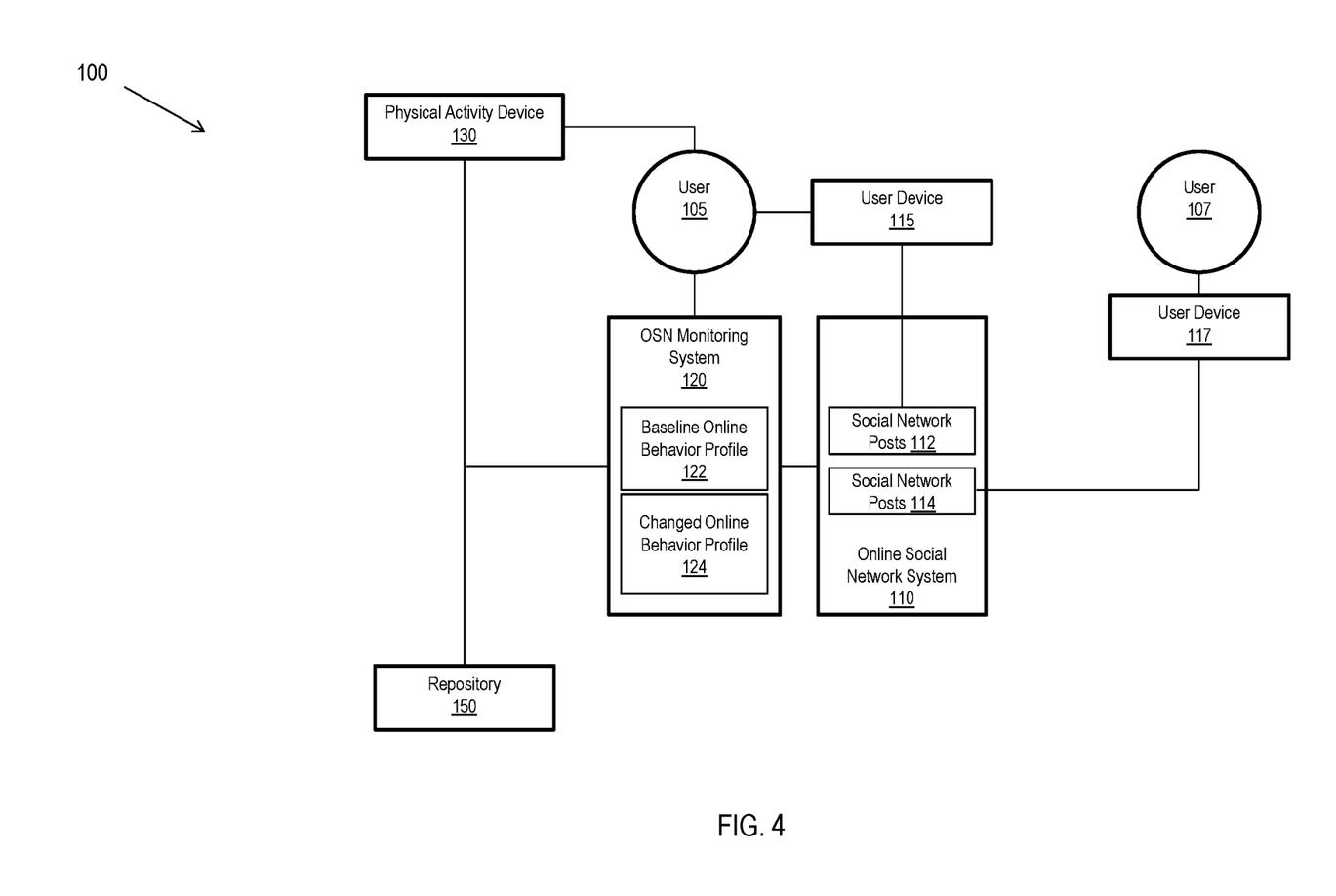
FIG. 4 depicts a system for online social network (OSN) monitoring to detect changes in online behavior for a user according to one or more embodiments of the present invention.

FIG. 4 depicts a system for online social network (OSN) monitoring to detect changes in online behavior for a user according to one or more embodiments of the present invention. Any/all of the components depicted in FIG. 4 can be a computing node 10 (FIG. 1). The depicted system 100 includes, among other components, an OSN system 110, such as FACEBOOK™, TWITTER™, REDIFF™, or any other online platform that facilitates a user 105 to enter/upload/publish social network posts 112. In one or more examples, the OSN system 110 includes multiple OSNs that user 105 uses. The user 105 transfers the post 112 onto the OSN system 110 via a user device 115, such as a tablet computer, a phone, a laptop computer, a desktop computer, or any other such communication device.

The system 100 further includes an OSN monitoring system 120, which continuously monitors the posts 112 that the user 105 adds to the OSN 110. In one or more examples, the OSN monitoring system 120 (also referred herein as a 'monitoring system') also monitors posts 114 that are added to the OSN 110 by another user 107 via a corresponding user device 117, where the posts 114 added by the other user 107 are directed to the first user 105. In one or more examples, the post 114 can be directed to the user 105 using one or more tags, by replying to a post 112 added by the user 105, by adding the post 114 to a page (e.g. FACEBOOK™ WALL) associated with the user 105, or in any other manner or a combination thereof. In one or more examples, the second user 107 can add the post 114 to a second OSN (e.g. TWITTER™) in response to the post 112 from the user 105 on a first OSN (e.g. FACEBOOK™).

By analyzing the posts 112 and the posts 114 on the OSN system(s) 110, the OSN monitoring system 120 creates a baseline online behavior (BOB) profile 122 and a change of behavior (COB) profile 124 for the user 105 at different time-points t1 and t2, respectively. The behavior profiles (BOB profile 122 and COB profile 124) are used to determine a change in the behavior of the user 105 between the two time-points t1 and t2. If a change is detected, a cause of the change is analyzed based on the posts 112 and the posts 114 using a taxonomy of life events that can be accessed from a repository 150.

The system 100 further includes the repository 150 that provides a taxonomy of keywords, each group in the taxonomy being associated with one or more life events. In one or more examples, the OSN monitoring system 120 builds the repository 150 as additional posts 112 and posts 114 are analyzed. The repository 150 is built by analyzing posts 112 and posts 114 from several users on the OSN system 110.

The OSN monitoring system 120 can further access physical activity data of the user 105 from one or more physical activity devices 130. A physical activity device 130 can include a fitness tracker, a heart rate monitor, a laugh-o-meter, a smart device (e.g. TV, speaker, phone, tablet etc.), a stress detector, a pedometer, a weighing scale, and the like. Data accumulated by such physical activity devices 130 is accessible by the OSN monitoring system 120, for example, through application programming interfaces using a communication network via one or more server computers. The physical activity data can include number of steps taken by the user 105, amount of time the user 105 has been physically active, amount of time the user 105 has slept, number of times the user 105 has laughed, movies/programs/advertisements that the user 105 has watched, music that the user 105 has listened, and other such data. The physical activity data can further include one or more biometrics of the user 105, such as, heart rate, weight, blood pressure, and the like.

Figure 5:
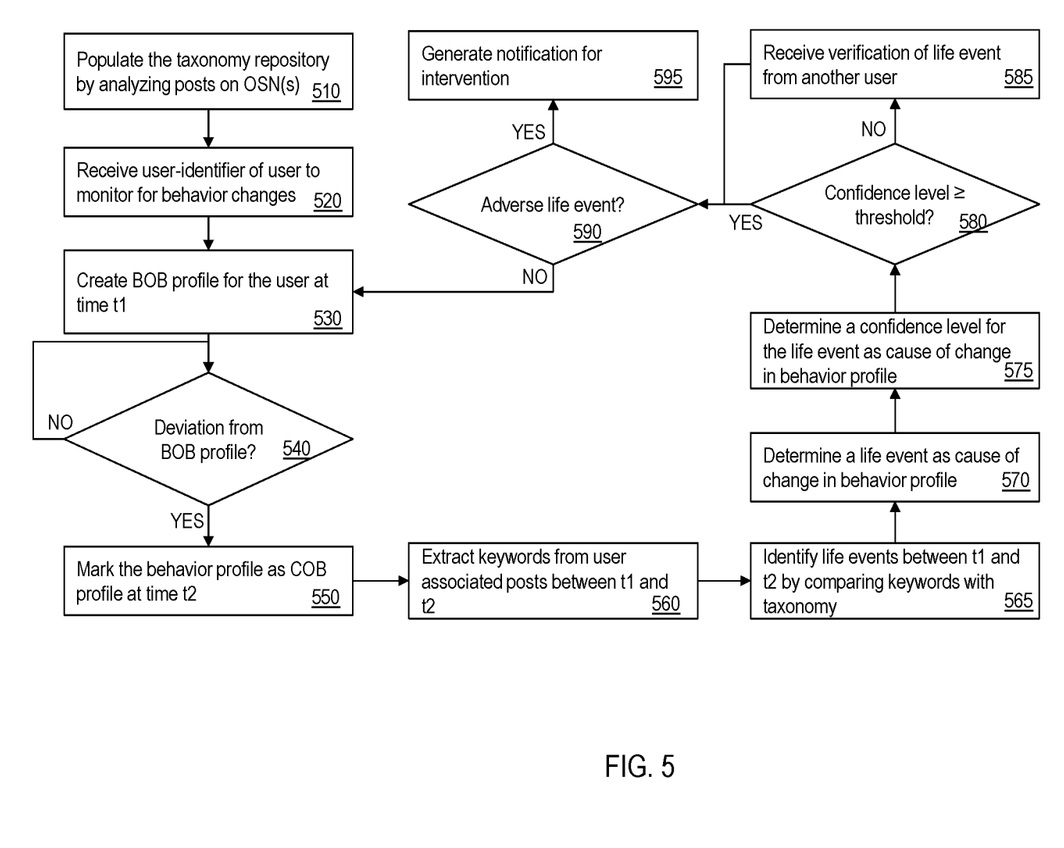
FIG. 5 depicts a flowchart of an example method for cognitive monitoring of online user profiles to detect changes in online behavior according to one or more embodiments of the present invention.

FIG. 5 depicts a flowchart of an example method for cognitive monitoring of online user profiles to detect changes in online behavior according to one or more embodiments of the present invention. The method includes populating the taxonomy repository 150, at 510. Populating the repository 150 includes analyzing existing social media posts on the OSN(s) 110 and extracting keywords from the social media posts that are associated with one or more life events. For example, keywords can be extracted from the social media posts using application programming interfaces (API) of services such as MONKEYLEARN™ and the like. Populating the repository 150 can be performed automatically using an artificial neural network, or any other machine learning technique, such as a supervised or unsupervised machine learning algorithm. The repository 150 can be populated, in one or more examples, using services such as IBM WATSON®. In one or more examples, a training dataset that includes manually identified keyword-life event associations is used by the machine learning algorithm to automatically populate the repository 150 using the social media posts in the OSN system(s) 110.

Figure 6:
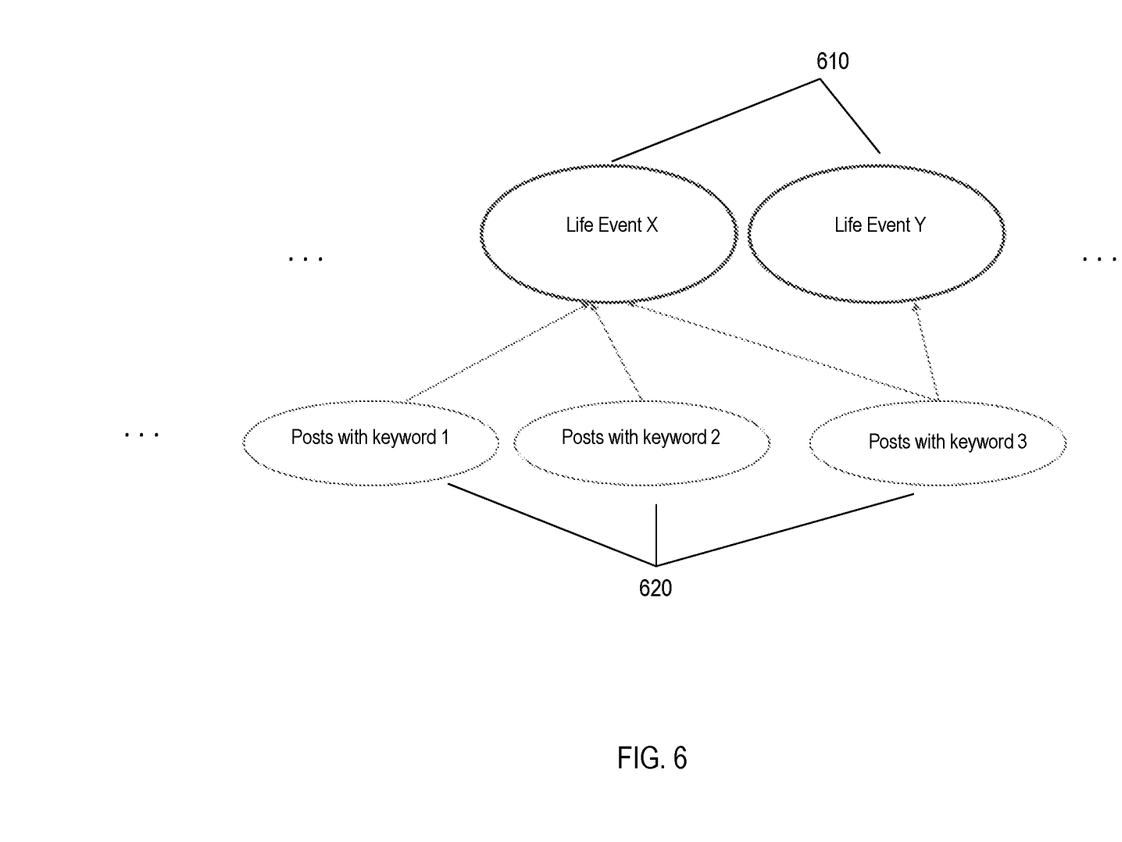
FIG. 6 depicts an example visualization of the taxonomy according to one or more embodiments of the present invention.

FIG. 6 depicts an example visualization of the taxonomy according to one or more embodiments of the present invention. One or more life events 610 are associated with one or more keywords 620 and/or social media posts including the keywords 620 in a many-to-many relationship. For example, the life events can include cyberbullying, marriage, birth, death, divorce, new relationship, new activity, new job, promotion, new school year, end of school year, and any other such event that can affect a person's behavior. The keywords can include one or more words (e.g. phrases) that are associated with the life events. For example, the keywords for cyberbullying can include, weird, ugly, fat, thin, hate, stay at home, and various other such words and phrases. In case of marriage, the keywords can include, ceremony, priest, wedding dress, ring, vows, and various other such words and phrases. The taxonomy of keywords 620 according to the corresponding life events 610 is stored in the repository 150.

The method further includes receiving a user identifier of the user 105 that is to be monitored for online social behavior change, at 520. In one or more examples, the user identifier can be provided by the user 105 himself/herself or by an acquaintance, such as a caretaker, family member, friend, employer, and the like. The method further includes creating the BOB profile 122 for the user 105, at 530. The BOB profile 122 is associated with a first time-point t1.

A behavior profile, either the BOB profile 122 or the COB profile 124, is generated by monitoring multiple configurable parameters for online behavior analysis, such as sentiment analysis, average frequency of usage, what time the user logs in, what time the user adds posts 112, which OSN system 110 the user 105 uses more often, which groups on the OSN system 110 does the user 105 frequently visit, and so on. It should be noted that the above are just a few examples of the data parameters that are monitored and included in the behavior profile, and that various other data parameters or factors can be used during implementation of one or more embodiments of the present invention.

Figure 7:
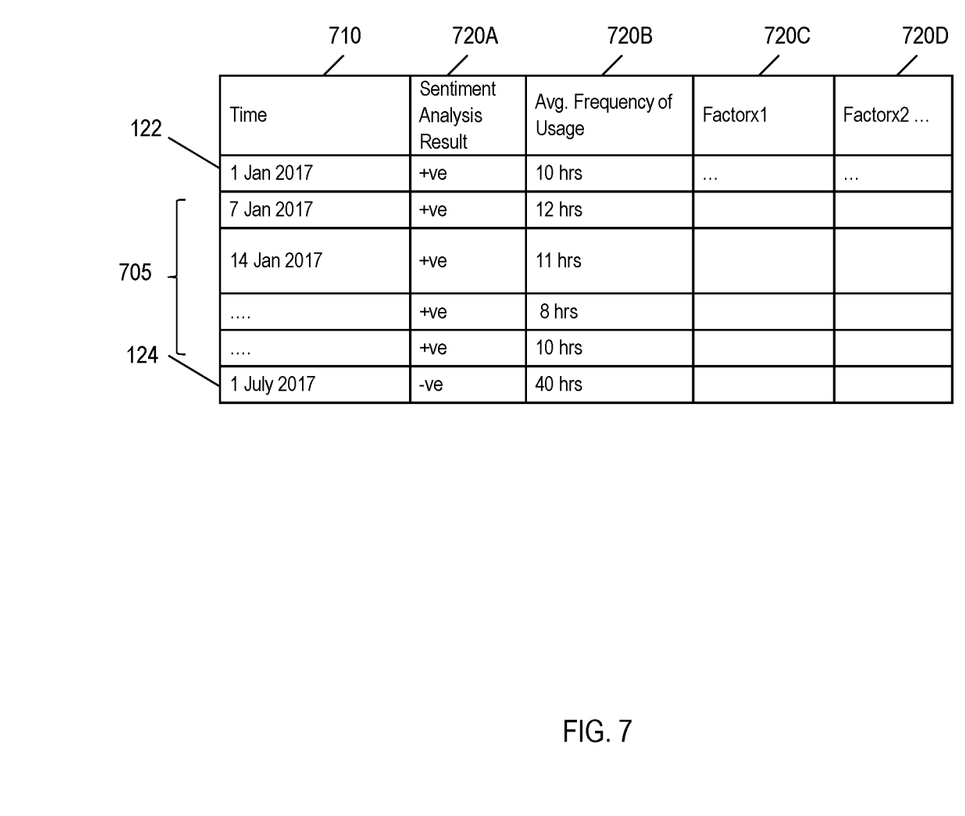
FIG. 7 depicts example behavior profiles according to one or more embodiments of the present invention.

FIG. 7 depicts example behavior profiles according to one or more embodiments of the present invention. The BOB profile 122 is created at the first time-point t1, indicated by column 710, and the COB profiles 124 are created at different time-points t2, t2>t1, again indicated by the column 710. The OSN monitoring system 120 also collects behavior profiles 705 for the user 105 in a continuous manner at a predetermined frequency as shown by the column 710. The frequency at which the behavior profiles 705 are collected can be configurable for each user 105.

Each behavior profile 705, 122, and 124 includes values for the data parameters 720, such as the sentiment analysis 720A, the average frequency of usage 720B, and other such factors, factor-1 720C, factor-2 720D, and so on. The data parameters that are used in the behavior profile for the user 105 are configurable and can vary from one user to another. The sentiment analysis 720A can be a binary value that indicates a sentiment in a post 112 (or 114) as being positive or negative. The sentiment analysis 720A can be obtained using services such as those from IBM™ that provide IBM Social Sentiment Index®, or from any other provider. Specifically, sentiment analysis is done through extraction of sentiments of users' posts 112/114, such as likes, dislikes, sad, angry smiley faces, or different types of content including text, videos, images, and the like.

Referring to the flowchart in FIG. 5 again, the method includes detecting a change from the BOB profile 122 in a behavior profile 705 for the user 105, at 540. Detecting the change includes continuously collecting behavior profiles 705 for the user 105 at a predetermined frequency, and comparing each collected behavior profile 705 with the BOB profile 122 that was collected at t1. If any of the data parameters 720 in the behavior profile collected at t2 changes by at least a predetermined threshold from the value in the BOB profile 122, the behavior profile 705 is marked as the COB profile 124, where a change was detected, at 550. For example, in the example scenario in FIG. 7, sentiment 710A changes from +ve to −ve at time t2 and the average frequency of usage 720B changes by more than a predetermined threshold. It should be noted that in other cases the changes can be detected in any other data parameters than those in the above example.

The method further includes extracting keywords from user associated posts between t1 and t2, at 560. The user associated posts include the posts 112 and the posts 114 from the OSN system(s) 110. Extracting the keywords includes parsing the posts 112/114 and performing syntactic/semantic analysis along with using the machine learning tools and APIs described herein, which were used to create the BOB profile 122.

Using the extracted keywords, life events for the user 105 are identified between the times t1 and t2 by comparing the keywords with the taxonomy in the repository 150, at 565. In one or more examples, the OSN monitoring system 120 correlates the extracted keywords with existing established patterns of life events that are grouped in the repository 150. Based on such correlating, the OSN monitoring system 120 identifies a life event 610 with which at least a certain percentage of the extracted keywords are associated. Alternatively, or in addition, the life event(s) 610 with which the highest percentage of the extracted keywords are associated are identified. The identified life event(s) 610 are deemed to be the cause of the change in the online social behavior of the user 105, at 570.

Further, the method includes determining a confidence level with which the determined life event 610 can be considered the cause of the change in the user's 105 online social behavior, at 575. Determining the confidence level includes correlating the online social activity data with user's 105 personal IoT network data. For example, the OSN monitoring system 120 accesses physical activity data from the one or more physical activity devices 130 such as a stress detector (e.g. ICALM™), laugh-o-meter (e.g. a number of laughs detected), a heart rate meter, a sleep monitoring device, a step counter, etc. A stress level of the user 105 is determined based on the physical activity data from the one or more physical activity devices 130. In one or more examples, alternative or additional indexes, other than the stress level, can be determined from the physical activity data. The OSN monitoring system 120 checks if the identified life event 610 and the stress level (or other indexes) from the physical activity data match at least within a predetermined threshold. A confidence level of the identified life event 610 being the cause of the change in the user's online social behavior is based on the match. If the confidence level is at least a predetermined threshold, for example, 65%, 75% or any other, one or more actions are taken based on a type of the identified life event 610.

If the confidence level is below the predetermined threshold, no action may be taken, or a notification may be generated for an acquaintance of the user 105 to verify the identified life event 610, at 585. For example, a notification/request is sent to another user to verify if the identified life event 610 has caused a change in the user's behavior. The other user can respond to the notification electronically to provide the verification.

If the identified life event 610 is one from a list of predetermined life events 610 that are considered to have an adverse effect on the mental and/or physical health of the user 105, a notification is sent to one or more acquaintances of the user 105 to intervene and help the user 105, at 590 and 595. For example, an adverse event can be that of bullying, cyberbullying, divorce, death, job loss, and the like.

The notification can be an email, a text message, an instant message, a phone call, a social media alert, or any other electronic or non-electronic communication. The notification can be sent to one or more designated caregivers or contacts for the user 105. For example, the user 105 may designate his/her spouse, sibling, parent, friend, doctor, employer, or any other acquaintance to receive the notification. Alternatively, or in addition, in case the OSN monitoring system 120 is used internally within an organization that the user 105 is employed with, the OSN system 110 being an internal OSN for the organization, the notification can be sent to human resource personnel, a manager, or any other designated person(s) in the organization.

If the life event 610 is not an adverse life event, which can adversely affect the user 105, the method is continued and the online behavior of the user 105 is monitored as described herein. For example, if the life event is a 'happy' event, such as marriage, birth, promotion, etc., or any other such event where an intervention is not required, no action may be taken.

In one or more examples, the BOB profile 122 is updated based on the latest behavior profile 705 of the user 105 (530).

Accordingly, one or more embodiments of the present invention facilitates improving the wellbeing of an online social platform user, for example by preventing suicides, depression, cyberbullying, and the like. The event detection described herein can also be used for targeted advertisement campaigns etc. Further, one or more embodiments of the present invention can incentivize online social activity time that is spent by the user by helping to improve the user's wellbeing. Identifying behavioral shifts can help protect victims and encourage learning opportunities for cyberbullies to realize the severity of their actions.

Because the OSN monitoring system 120 continuously monitors the OSN systems 110 to update the taxonomy and the monitor the social media posts 112/114, the OSN monitoring system 120 learns new lingo through self-learning that helps identify and update the user's BOB profile 122. When new patterns emerge the system learns and adjusts to remain useful.

Figure 8:
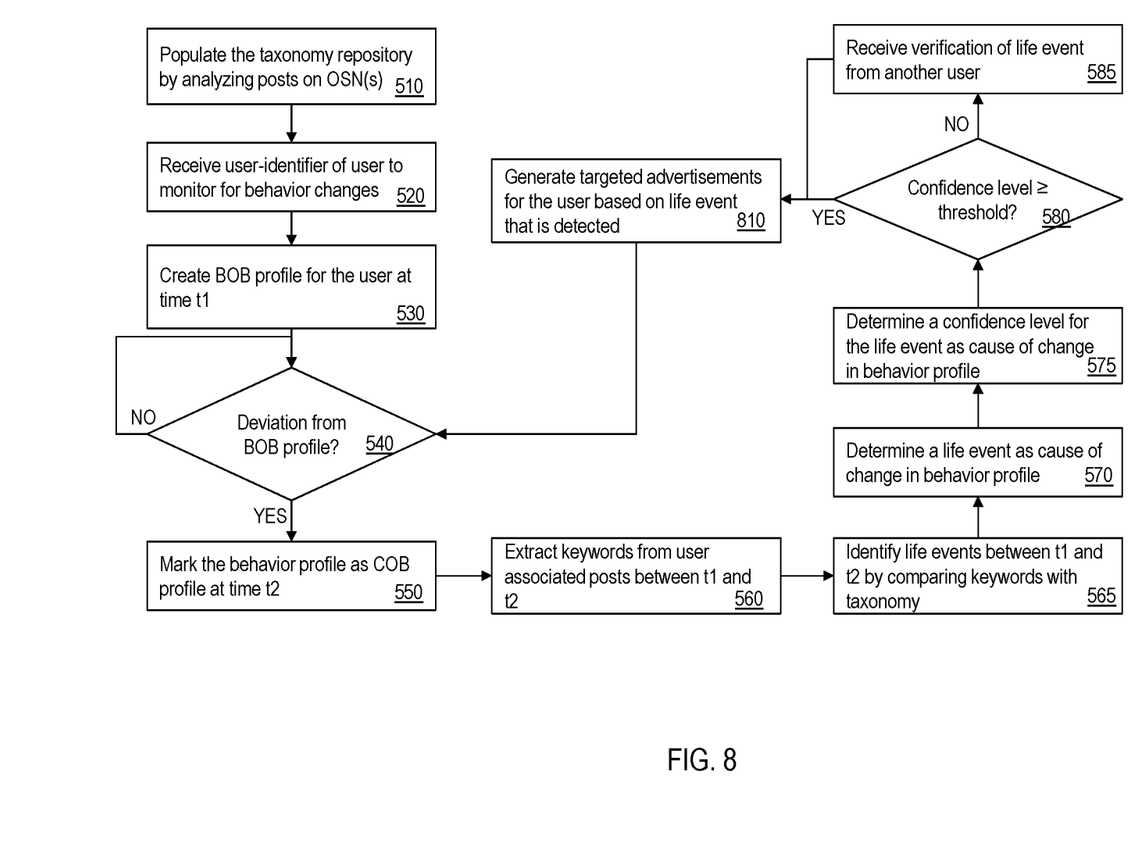
FIG. 8 depicts a flowchart for a method of providing targeted marketing campaign or advertisements to a user according to one or more embodiments of the present invention.

FIG. 8 depicts a flowchart for a method of providing targeted marketing campaign or advertisements to a user according to one or more embodiments of the present invention. The method includes the operations described herein with reference to FIG. 5, which are not repeated herein, to detect a life event as a cause of an online behavior change of the user 105 with at least a certain confidence level (580). In this case, once the life event 610 is identified, an advertisement system 140 generates or selects advertisements and other marketing material specific for the life event 610 and for the user 105, at 810. The targeted marketing material may be incorporated into the posts 114 that are directed to the user 105. For example, the targeted marketing material can include text, images, video, and other such electronic content. Alternatively, or in addition, the advertisement system 140 can generate marketing material for the consumption of the user 105 across other types of media, such as email, streaming audio, streaming video, paper mail, and the like based on the life event 610. For example, if the life event 610 is that of the user 105 getting promoted, the marketing content may include advertisements for clothes, shoes, and the like for the user 105 to have a wardrobe change. Alternatively, or in addition, in the case of the life event 610 being that of death, or divorce, the marketing material may include advertisements for services such as counselors.

Accordingly, one or more embodiments of the present invention can be used to monitor an internal social network within an organization that employs multiple employees who use the internal social network. Typically, an employee's well-being is important for the organizations, and detecting a change in employee's social activity over the Organisational Social Network can help managers to look after their employees and intervene as required to facilitate monitoring and trying to rectify any deterioration in the employee's mental health.

Alternatively, or in addition, one or more embodiments of the present invention can facilitate online social networks such as TWITTER™, FACEBOOK™ and the like to be used as a useful source of information for digital marketers, by monitoring of which a marketing service provider can detect a change in behavior for existing or potential customers. The marketing service provider can subsequently provide digital marketing and personalize marketing campaigns for their customers based on detecting life events using the online social network data.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s).

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. A computer-implemented method comprising:
    creating a baseline online behavior profile of a user at a time t1 based on a usage of a social network by the user;
    continuously monitoring an online behavior profile of the user on the social network;

in response to detecting a deviation between the online behavior profile and the baseline online behavior profile, creating a changed online behavior profile of the user at a time t2, t2>t1;

extracting keywords from a plurality of online posts associated with the user, the online posts being from time t1 until time t2;

determining an event associated with the extracted keywords;

determining a confidence level for the event as cause of the deviation between the online behavior profile and the baseline online behavior profile by comparing the event with a measurement of stress level of the user from one or more activity monitoring devices of the user, where the confidence level is based on the stress level being within a predetermined range that is associated with the event;

in response to the confidence level being below a predetermined threshold, corroborating an occurrence of the event that is determined by receiving a verification from a second user, wherein the second user verifies that the event occurred via an electronic confirmation; and in response to the corroboration from the second user, and in response to the event being of a predetermined type, sending a notification to a designated caretaker of the user.

2. The computer-implemented method of claim 1, wherein the event is detected by correlating the extracted keywords with a taxonomy repository of keywords and events.

3. The computer-implemented method of claim 2, wherein the taxonomy repository is generated by analyzing a plurality of online posts.

4. The computer-implemented method of claim 1, wherein the deviation between the online behavior profile and the baseline online behavior profile is detected based on a change in at least one data parameter from a plurality of data parameters from the online behavior profile.

5. The computer-implemented method of claim 4, the online behavior profile comprising a sentiment analysis, and an average frequency of usage of the social network by the user.

6. The computer-implemented method of claim 1, further comprising generating content specifically for the user based on the event.

7. A system comprising:
an online social network;
a memory; and
a processor configured to monitor the online social network for a change in online behavior of a user when using the online social network by performing a method comprising:
  creating a baseline online behavior profile of a user at a time t1 based on a usage of a social network by the user;
  continuously monitoring an online behavior profile of the user on the social network;
  in response to detecting a deviation between the online behavior profile and the baseline online behavior profile, creating a changed online behavior profile of the user at a time t2, t2>t1;
  extracting keywords from a plurality of online posts associated with the user, the online posts being from time t1 until time t2;
  determining an event associated with the extracted keywords;
  determining a confidence level for the event as cause of the deviation between the online behavior profile and the baseline online behavior profile by comparing the event with a measurement of stress level of the user from one or more activity monitoring devices of the user, where the confidence level is based on the stress level being within a predetermined range that is associated with the event;
  in response to the confidence level being below a predetermined threshold, corroborating an occurrence of the event that is determined by receiving a verification from a second user, wherein the second user verifies that the event occurred via an electronic confirmation; and
  in response to the corroboration from the second user, and in response to the event being of a predetermined type, sending a notification to a designated caretaker of the user.

8. The system of claim 7, wherein the event is detected by correlating the extracted keywords with a taxonomy repository of keywords and events.

9. The system of claim 8, wherein the taxonomy repository is generated by analyzing a plurality of online posts.

10. The system of claim 7, wherein the deviation between the online behavior profile and the baseline online behavior profile is detected based on a change in at least one data parameter from a plurality of data parameters from the online behavior profile.

11. The system of claim 10, the online behavior profile comprising a sentiment analysis, and an average frequency of usage of the social network by the user.

12. The system of claim 7, wherein the method further comprises generating content specifically for the user based on the event.

13. A computer program product comprising a computer readable storage medium having stored thereon program instructions executable by one or more processing devices to perform a method comprising:
  creating a baseline online behavior profile of a user at a time t1 based on a usage of a social network by the user;
  continuously monitoring an online behavior profile of the user on the social network;
  in response to detecting a deviation between the online behavior profile and the baseline online behavior profile, creating a changed online behavior profile of the user at a time t2, t2>t1;
  extracting keywords from a plurality of online posts associated with the user, the online posts being from time t1 until time t2;
  determining an event associated with the extracted keywords;
  determining a confidence level for the event as cause of the deviation between the online behavior profile and the baseline online behavior profile by comparing the event with a measurement of stress level of the user from one or more activity monitoring devices of the user, where the confidence level is based on the stress level being within a predetermined range that is associated with the event;
  in response to the confidence level being below a predetermined threshold, corroborating an occurrence of the event that is determined by receiving a verification from a second user, wherein the second user verifies that the event occurred via an electronic confirmation; and in response to the corroboration from the second user, and in response to the event being of a predetermined type, sending a notification to a designated caretaker of the user.

14. The computer program product of claim 13, wherein the event is detected by correlating the extracted keywords with a taxonomy repository of keywords and events, the taxonomy repository is generated by analyzing a plurality of online posts.

15. The computer program product of claim 13, wherein the deviation between the online behavior profile and the baseline online behavior profile is detected based on a change in at least one data parameter from a plurality of data parameters from the online behavior profile.

16. The computer program product of claim 15, the online behavior profile comprising a sentiment analysis, and an average frequency of usage of the social network by the user.

17. The computer program product of claim 13, the method further comprising generating content specifically for the user based on the event.

* * * * *